US00PP35785P3

(12) United States Plant Patent
Olesen et al.

(10) Patent No.: US PP35,785 P3
(45) Date of Patent: Apr. 30, 2024

(54) ***CLEMATIS* PLANT NAMED 'EVIPO117'**

(50) Latin Name: *Clematis viticella*
Varietal Denomination: Evipo117

(71) Applicants: Mogens Nyegaard Olesen, Fredensborg (DK); Raymond J. Evison, Braye Vineries Guernsey (GB)

(72) Inventors: Mogens Nyegaard Olesen, Fredensborg (DK); Raymond J. Evison, Braye Vineries Guernsey (GB)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 18/445,489

(22) Filed: Sep. 8, 2023

(65) Prior Publication Data

US 2024/0057490 P1 Feb. 15, 2024

(30) Foreign Application Priority Data

Sep. 30, 2022 (QZ) ..... PBR 20222181

(51) Int. Cl.
*A01H 5/02* (2018.01)
*A01H 6/72* (2018.01)

(52) U.S. Cl.
USPC ..... Plt./228
CPC ..... *A01H 6/72* (2018.05)

(58) Field of Classification Search
USPC ..... Plt./228
CPC ..... A01H 5/02
See application file for complete search history.

(56) References Cited

PUBLICATIONS

CPVO Application Consultation Version 4.12.17 Citation for 'Evipo117'; Nov. 28, 2023; 3 pages.*

* cited by examiner

*Primary Examiner* — Kent L Bell

(57) ABSTRACT

A new *Clematis* plant with a moderately compact growth habit, profuse, violet blue flowers, and continuous summer flowering. The variety successfully propagates from softwood cuttings and is suitable for cultivation in commercial nursery culture. This new and distinct variety has shown to be uniform and stable in the resulting generations from asexual propagation from vegetative cuttings.

2 Drawing Sheets

Botanical Classification: Genus: *Clematis*. Species: *viticella*.

Variety Denomination: 'Evipo117'.

This application claims priority to Plant Breeder's Rights Application Number 2022/2181, which was filed at the Community Plant Variety Rights Office in the European Union on Sep. 30, 2022, the contents of which are hereby incorporated by reference for all purposes.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling. Both parent varieties are non-patented.

The two parents were crossed during the summer of 2005 and the resulting seeds were planted the following winter in a controlled environment in Guernsey, Channel Islands, United Kingdom. The new variety named 'Evipo117' originated as a single seedling from the stated cross.

The new *Clematis* plant may be distinguished from its female seed parent and male pollen parent by the following characteristics. The female seed parent has light pink flowers while the new variety has violet blue tepals with a purple bar stripe. The male seed parent has dark violet blue tepals with no central bar while the new variety has violet blue tepals with a purple bar stripe.

The objective of the hybridization of this *Clematis* plant was to create a new and distinct variety for nursery culture with unique qualities such as:

1. Uniform and abundant violet blue flowers;
2. Vigorous and moderately compact growth, making the variety suitable for container culture; and
3. Improved disease resistance; and
4. Flowering heavily from new growth.

This combination of qualities was lacking in *Clematis* plants that were in commercial cultivation and the qualities have been substantially achieved in the new variety.

'Evipo117' was selected by Mogens N. Olesen and Raymond J. Evison in their *Clematis* development program in the Channel Islands, United Kingdom in 2006. Asexual reproduction of 'Evipo117' by means of vegetative cuttings and traditional layering was first performed by Mogens N. Olesen and Raymond J. Evison in the nursery located in Guernsey UK, during the summer of 2006. This initial and subsequent asexual propagations have demonstrated that the characteristics of 'Evipo117' are true to type and are transmitted from one generation to the next.

BRIEF DESCRIPTION OF THE DRAWING

The accompanying color illustrations show as true as is reasonably possible to obtain in color photographs of this type the typical characteristics of the buds, flowers, leaves, and stems, of 'Evipo117'.

Specifically illustrated in FIG. 1 of the drawings are open flowers viewed from above, tepals detached, a flower bud and side view of flowers upon opening.

DETAILED DESCRIPTION OF THE VARIETY

Figure 1:
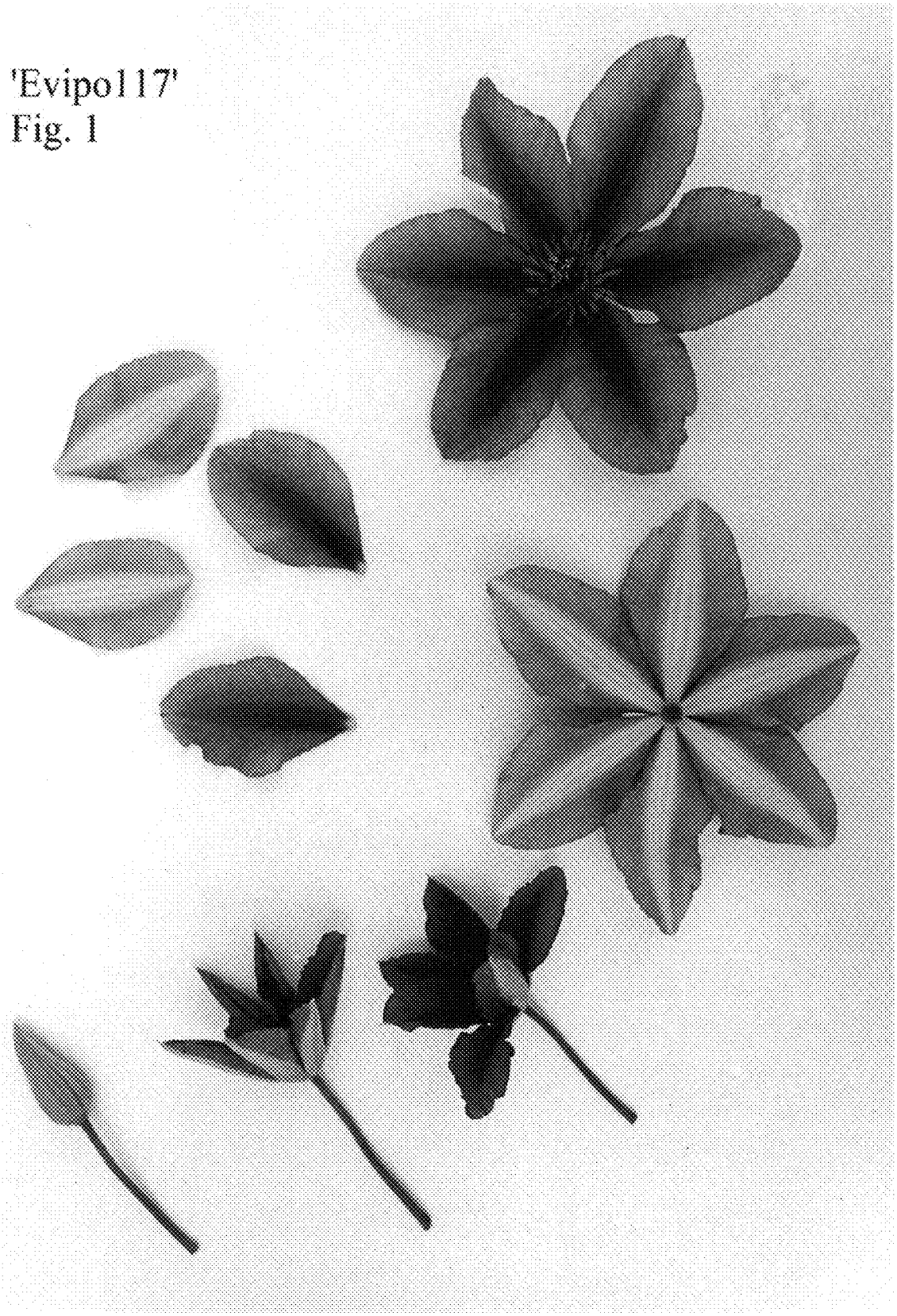
Figure 2:
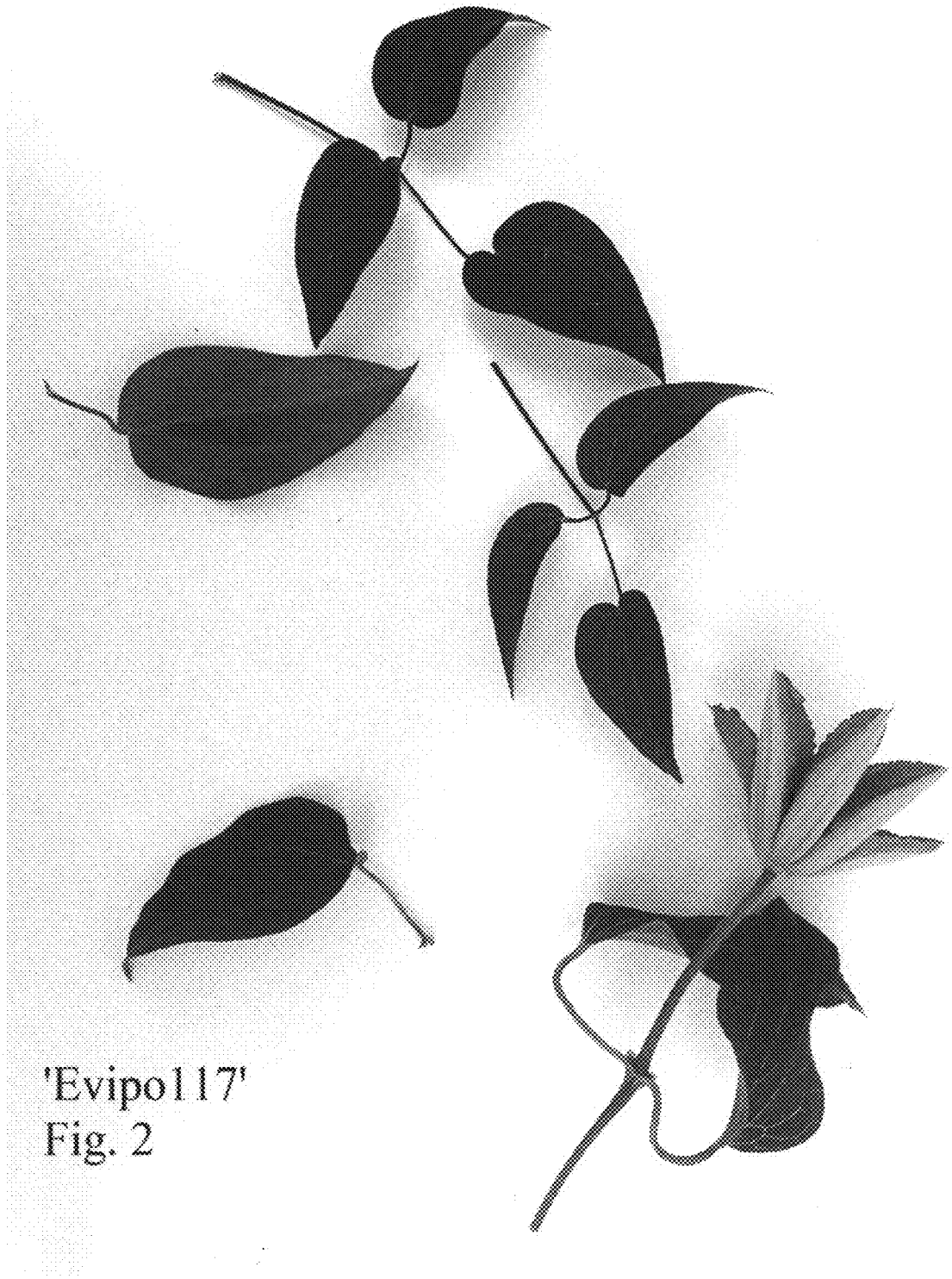
FIG. 2 shows mature compound leaves, and a single flower attached to the vine. The illustrated plants are 2 years of age.

The following is a detailed description of 'Evipo117', as observed in its growth throughout the flowering period in Odense Denmark. Observed plants were cultivated outdoor for a period of 24 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *Clematis* variety 'Evipo059' described and illustrated in U.S. Plant Pat. No. 28,671 are compared to 'Evipo117'. While 'Evipo117' has an open flower diameter of 115 mm, 'Evipo059' has a flower diameter of 100 mm. The claimed plant has an upper surface tepal colour of Violet Group 85A and 85B with a central bar stripe that is a combination of Purple Group N77A and Purple Group 77A while 'Evipo059' is Violet Group N88B with a central bar of Purple Group N79C.

Flower and Flower Bud

Blooming habit: Continuous. The natural flowering period is generally from April to September.

Flower bud:
- *Size.*—Normally 35 mm in length. Bud diameter is 12 mm.
- *Bud form.*—Long campanulate, broad based.
- *Bud color.*—Yellow-Green Group 145C.
- *Texture.*—Pubescent.

Pedicel:
- *Surface texture.*—Smooth.
- *Length.*—On average 26 mm in length with 2 mm diameter.
- *Color.*—Yellow-Green Group 145A.
- *Strength.*—Moderately strong.

Receptacle:
- *Surface texture.*—Lightly pubescent.
- *Shape.*—Broad funnel.
- *Size.*—1 mm (h)×2 mm (w).
- *Color.*—Yellow-Green Group 145A.

Flower arrangement:
- *Location on vine.*—Flowering on new growth.
- *Borne.*—Singly and in clusters of 5 to 7 flowers.

Flower bloom:
- *Size.*—On average, flowers are 115 mm in diameter and 20 mm in depth.
- *Profile.*—Flat.
- *Fragrance.*—None.
- *Lasting quality.*—Flowers normally remain up to 10 days on the plant.

Tepals:
- *Tepal color.*—Upon opening the upper surface is a blend of Violet Group 83C and Purple Group N79D with a central bar stripe of Purple Group N77A. The lower surface upon opening is Violet Group 83D with a central bar stripe Yellow-Green Group 145D. After opening, the upper surface is a blend of Violet Group 85A and 85B with a central bar stripe that is a combination of Purple Group N77A and Purple Group 77A. The lower surface is Violet-Blue Group 91B with a central bar stripe the color of Green-White Group 157B.
- *Quantity.*—Normally 6 tepals.
- *Size.*—About 55 mm in length by 35 mm wide.
- *Shape.*—Individual tepal shape is spathulate. The tepal apex is rounded with a very fine point. The tepal base acute.
- *Apex recurvature.*—Light.
- *Tepal cross section.*—Flat.
- *Margins.*—Entire. Strong undulations of margin observed.
- *Persistence.*—Tepals drop off cleanly.

Reproductive organs:
- *Pollen.*—None observed.
- *Anthers.*—Size: 6 mm in length. Color: Purple Group 79A. Quantity: About 35.
- *Filaments.*—Color: White Group 155B. Length: 7 mm.
- *Pistils.*—Quantity: On average 25. Length: About 8 mm. Styles: Greyed-Purple Group N187A. Stigmas: White Group 155A. Superior in location relative to the length of filaments and the height of the anthers.

Seed head characteristics: Seed not observed to date.

Plant

Plant form: Climbing.

Plant growth: Moderately compact.

Size: Seasons growth attains 100 cm in height on average. Spread is about 50 cm.

Stems:
- *Color.*—Juvenile stems are Yellow-Green Group 144B. Mature stems are Yellow-Green Group 144A.
- *Internodes.*—On average, 6 cm between nodes.
- *Length.*—About 30 cm from the base of the plant to the flowering portion of the stem.
- *Diameter.*—About 3 mm.
- *Texture.*—Mature stems are smooth.

Plant foliage:
- *Leaf characteristics.*—Deciduous.
- *Arrangement.*—Ternate.
- *Leaf size.*—Compound leaves are about 150 mm (l)× 130 mm (w). Leaflets range from 50 to 80 mm (l)×20 to 40 mm (w).
- *Abundance.*—1 or 2 leaves per 10 cm of stem.
- *Leaflet color.*—Juvenile upper Yellow-Green Group 144B. Juvenile lower Yellow-Green Group 144B. Mature upper Yellow-Green Group 146A. Mature lower Yellow-Green Group 147C.
- *Stipules.*—Absent.
- *Petioles.*—Size: Normally 60 to 70 mm in length by 2 mm diameter. Texture: Smooth. Color: Greyed-Purple Group 187A.
- *Petioloule.*—Size: About 15 mm in length by 1.5 mm diameter. Texture: Smooth. Color: Greyed-Purple Group 187A.
- *Leaflet shape.*—Cordate. The base is rounded, or oblique. The apex is acute.
- *Margin.*—Entire.
- *Surface.*—The upper side is smooth, the lower side is smooth.
- *Thickness.*—Moderate.
- *Glossiness.*—Moderately glossy.

Disease resistance: Subject to any disease that normally attacks the species. However the variety is more tolerant to *Clematis* wilt, *Ascochyta clematidina*, than some *Clematis* known to the inventors.

Cold hardiness: The variety is tolerant to USDA Hardiness Zone 6.

Heat tolerance: The variety has been found to be suitable for climate conditions found in The American Horticulture Society heat zone 7.

We claim:

1. A new and distinct variety of *Clematis* plant named 'Evipo117', substantially as described and illustrated herein.

* * * * *

'Evipo117'

'Evipo117'